United States Patent [19]

Slinkman et al.

[11] Patent Number: 5,065,103
[45] Date of Patent: Nov. 12, 1991

[54] SCANNING CAPACITANCE - VOLTAGE MICROSCOPY

[75] Inventors: James A. Slinkman, Montpelier, Vt.; Hemantha K. Wickramasinghe, Chappaqua; Clayton C. Williams, Peekskill, both of N.Y.

[73] Assignee: International Business Machines Corporation, Armonk, N.Y.

[21] Appl. No.: 499,857

[22] Filed: Mar. 27, 1990

[51] Int. Cl.⁵ .............................................. G01R 29/12
[52] U.S. Cl. ................................... 324/458; 324/662; 324/158 R
[58] Field of Search ...................... 324/662, 663, , 689, 324/158 R, 458, 671; 250/306

[56] References Cited

U.S. PATENT DOCUMENTS

| Re. 32,457 | 7/1987 | Matey | 369/58 |
|---|---|---|---|
| 4,378,699 | 4/1983 | Wickramasinghe | 73/606 |
| 4,464,627 | 8/1984 | Munakata et al. | 324/158 R |
| 4,747,698 | 5/1988 | Wickramasinghe et al. | 374/6 |
| 4,797,620 | 1/1989 | Williams | 324/458 |
| 4,891,584 | 1/1990 | Kamienicki et al. | 324/158 R |
| 4,935,700 | 6/1990 | Garbini et al. | 324/662 |
| 4,941,753 | 7/1990 | Wickramasinghe | 324/158 D |
| 4,992,659 | 2/1991 | Abraham et al. | 324/158 P |

OTHER PUBLICATIONS

"Lateral Dopant Profiling with 200 nm Resolution by scanning Capacitance Microscopy," by C. C. Williams, et al., Appl. Phys. Lett. 55 (16) (16 Oct. 1989), p. 1662.
"Scanning Capacitance Microscopy on a 25 nm Scale," by C. C. Williams, et al., Appl. Phys. Lett. 55(2), 10 Jul. 1989, pp. 203-205.
"An Experimental Scanning Capacitance Microscope," by H. P. Kleinkencht, et al., Scanning Microscopy, vol. 2, No. 4, (1988), pp. 1839-1844.
"High Resolution Capacitance Measurement and Potentiomentry by Force Microscopy," by Y. Martin, et al., App. Phy. Lett. 52, 1103 (1988).
"Scanning Capacitance Microscopy," by Bugg, J. Phys. E. Sci. Instrum. 21 (1988) 147-151.
"Scanning Capacitance Microscopy," J. R. Matey, et al., J. Appl. Phys. 57 (5), 1 Mar. 1985, pp. 1437-1444.
"Capacitance—Pick-Up Circuitry for Video Disks," by R. C. Palmer, et al., RCA Rev. 43, 194 (1982).
Industrial Apportunities Ltd. Potential Measuring System.

Primary Examiner—Kenneth A. Wieder
Assistant Examiner—Maura K. Regan
Attorney, Agent, or Firm—J. Dennis Moore

[57] ABSTRACT

An apparatus and method for generating microscopic scan data of C-V and/or dC/dV over a scan area. A scanning microscope, for example a scanning force microscope, is provided with a voltage biased tip, for example, of tungsten, which is scanned across an area to derive the data. The data can be used to derive a plot of semiconductor dopant level across the scan area. Other material properties can be derived, for example, carrier generation and recombination rates and subsurface defects.

19 Claims, 5 Drawing Sheets

SCANNING CAPACITANCE - VOLTAGE MICROSCOPY

BACKGROUND OF THE INVENTION

1. Field of the Invention

The present invention relates generally to method and apparatus for determining material properties by microscopic scanning, and more particularly relates to determination of material properties including dopant profiles of materials, using capacitance-voltage techniques.

2. Background Art

Present day very large scale integrated (VLSI) circuits technology demands accurate knowledge of the spatial extent in three dimensions (3D) of active impurity dopants which have been incorporated into the discrete device elements. The devices are predominantly either bipolar or metal oxide semiconductor field effect (MOSFET) transistors, diodes, or capacitors. A typical device occupies an area of the order of 10 $\mu m^2$. The active region of such a device, where most current flows, is engineered by incorporating dopants, for example arsenic, boron, or phosphorous, in a concentration range of $10^{15}$ to $10^{20}$ cm$^{-3}$. It is necessary to control the variation, or profile, of impurity dopants to a spatial resolution of 100 nm or less for high yield in manufacture and for reliability of the circuitry in the field. On the other hand, lack of precision related to the incorporation of impurity dopants can result in a proliferation of undesirable defects during later steps in the manufacturing process, and/or less than adequate device performance, or even device failure. Such high precision in the characterization of dopant profiles on a microscopic scale is, clearly, highly desirable for efficient device design. In order to achieve predictability in device behavior, one must be able to measure accurately the dopant profiles and feed this information back into the design cycle. However, heretofore it has been impossible to achieve this high precision, except in 1D, either in the design or manufacturing phases of VLSI components on the submicron scale.

Current techniques for quantitative measurement of dopant profiles are limited to high resolution in one dimension only. Such techniques include Secondary-Ion Mass Spectroscopy (SIMS), Spreading Resistance (SR), and macroscopic Capacitance-Voltage (C-V). For example, see S.M. Sze, "VLSI Technology" McGraw-Hill Book Co., New York (1983, see for example, Chapters 5 and 10). Other, non-quantitative methods exist, for example S.T. Ahn and W.A. Tiller, J. Electrochem. Soc. 135, 2370 (1988) and M.C. Roberts, K.J. Yellup and G.R. Booker, Institute of Physics Conference Series No. 76, No. 11 (Institute of Physics, London, 1985). In one dimension (1D) of the quantitative methods, only C-V satisfies the three criteria outlined above. However, as mentioned above, the data is provided in a single dimension only, and over a broad area.

Figure 1:
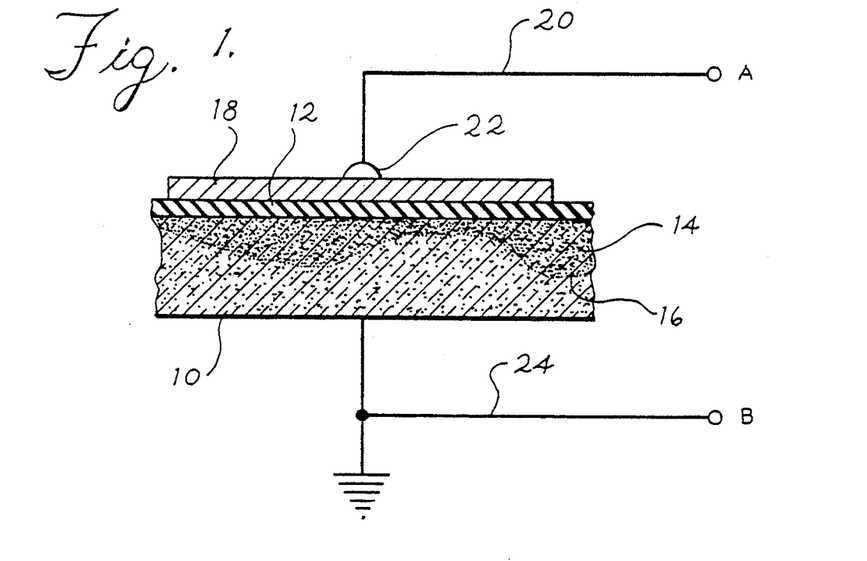
FIG. 1 is a cross sectional diagram of a semiconductor material having a capacitive plate disposed thereon for one dimensional C-V measurements.

For example, referring to FIG. 1, a cross section of a portion of semiconductor material 10 is shown, having an oxide layer 12 thereon and a doped region 14, the extent of which within semiconductor material 10 being shown by dashed line 16. A capacitive plate 18 is bonded to the oxide 12, and an electrode 20 is contracted to plate 18. Semiconductor material 10 is also grounded by way of a second electrode 24.

Ports A and B, of electrodes 20 and 24, respectively, are connected to a C-V meter. C-V measurements are made according to the technique, for example, of Nicollian and Brews, "MOS Physics and Technology", (Wiley, New York, 1982), p. 383, and the average dopant level underneath the plate 18 is derived. Typical dimensions for this kind of measurement are an oxide 12 thickness of approximately 20 nm, a plate 18 thickness of approximately 500 nm, a semiconductor material 10 thickness of approximately one millimeter, and an average dopant region 14 depth of approximately 1000 nm. The lateral extent of plate 18 is typically approximately of the order of a millimeter.

The limitations of the technique are readily apparent. Dashed line 16 in FIG. 1 represents the variations in the depth of dopant region 14. This region 14 has a varying depth, determined, for example, by boundaries between semiconductor devices within an integrated circuit. The measurement provided by the above scheme only provides gross average information about the vertical dopant density, and reveals nothing about lateral dopant profile in such cases.

In addition, though the lateral extent of dopant is of equal importance in device design to dopant depth, heretofore it could only be inferred through clever experimentation and extrapolation of 1D measurements, or, after the fact, through device performance. See for example P.M. Fahey, P.B. Griffin and J.D. Plummer, Rev. Mod. Phys. Vol. 61, 289 (1989), and E.H. Nicollian and J.R. Brews, above.

SUMMARY OF THE INVENTION

In accordance with the present invention a method and apparatus are provided for determining properties of a material. A fine tip is moved in close proximity to a surface of the material within a predetermined area, and a voltage is applied to the tip with respect to the material. The value of a parameter corresponding to the capacitance in a region of the material near the tip, for example, force, is sensed for a given position of the tip, and for a plurality of voltage levels. The tip is moved across the area and voltage and capacitance value data is collected for a number of positions of the tip across the area, or continuously. Finally, the data is related according to a predetermined relationship to derive the desired material property at each of the tip positions within the area.

The data thus derived can be used to advantageously create a profile of important material properties. For example, according to one aspect of the present invention a plot of the dC/dV signal obtained by the application of the present invention may be used to derive the profile of dopant level of a region of a VLSI circuit in a semiconductor material. To the inventors' knowledge, this has heretofore been impossible.

Other material properties may be derived as well. For example, according to a further aspect of the present invention a modulated laser light may be shined upon the area of a semiconductor material being scanned, or, alternatively, a bias voltage may be applied across the area being scanned, and carrier generation and recombination may be derived from the aforementioned data. In addition, charge may be applied to a semiconductor material, and subsurface defects may be derived, again using a plot of the aforementioned data. Numerous other material properties may also be obtained similarly, for example, oxide thickness, etc.

BRIEF DESCRIPTION OF THE DRAWINGS

FIG. 3A is a cross sectional diagram through a semiconductor material showing, the relationship of the material to a fine tungsten tip in the practice of the preferred embodiment of the present invention, while FIG. 3B shows the effective capacitances associated with the arrangement of FIG. 3A.

DETAILED DESCRIPTION OF THE PREFERRED EMBODIMENT

The preferred embodiment of the present invention fulfills all of the above criteria for dopant density profiling in 3D. According to the preferred embodiment, the near-field of a microscopic, non-contacting, conducting, scannable probe under electrical bias is used to deplete a localized region of the semiconductor sample in the vicinity of the probe. The tip of the probe is nonplanar and has a radius of curvature on the order of ten angstroms to ten microns. The measured depletion capacitance provides the necessary information to determine the local, activated dopant density. This is achieved by means of a deconvolution algorithm described below. The size and shape of the probe essentially dictate the submicron resolution of the apparatus.

Figure 2:
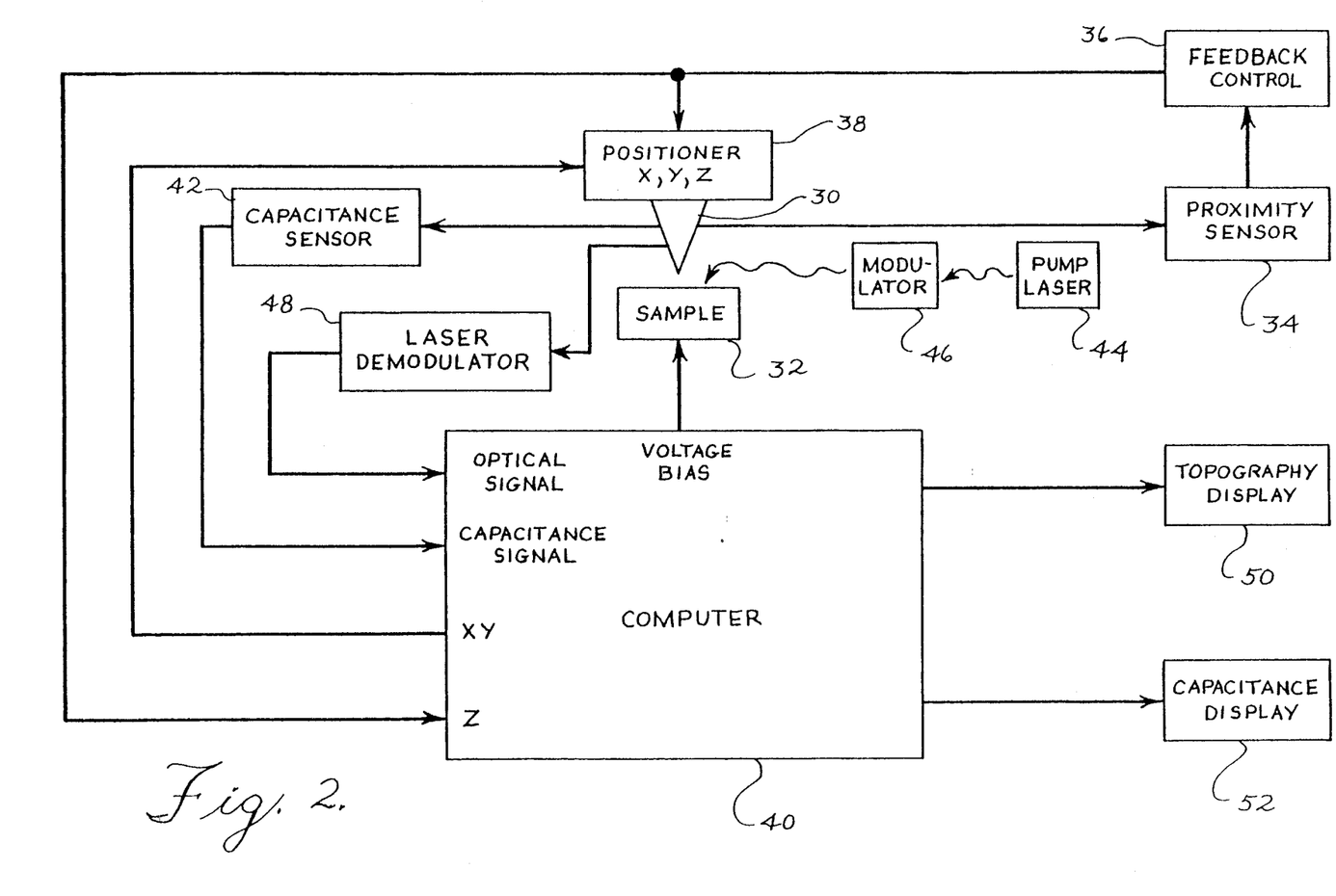
FIG. 2 is a block diagram showing the essential elements of the preferred embodiment of the present invention.

FIG. 2 is a block diagram showing the basic elements of the preferred embodiment of the present invention. A fine metallic tip 30 is suspended over a sample 32 of semiconductor material, and a computer 40 provides a voltage bias between tip 30 and sample 32. A proximity sensor 34 senses the spacing between tip 30 and sample 32, and provides a signal indicative thereof to feedback control 36. Feedback control 36 generates a signal which is applied to a positioner 38 so as to maintain the relative spacing between tip 30 and sample 32 constant. This signal is also applied to computer 40 to provide an indication of the topographic variations of the surface of sample 32. Computer 40 provides a further signal to positioner 38 to control movement of tip 30 across the surface of sample 32, that is, in the XY directions. In this way tip 30 can be scanned across sample 32, for example.

A pump laser 44 provides a laser light output to a light modulator 46. The light output of modulator 46 can be shined on the surface of sample 32 in the region of proximity of tip 30. A laser demodulator 48 monitors a signal corresponding to the sensed capacitance at the frequency at which the modulator 46 modulates the laser light from pump laser 44, and provides an input signal to computer 40. A capacitance sensor 42 monitors the capacitance of the tip 30, air, sample 32 system and provides a output signal representative of that capacitance which is applied to computer 40.

A topography display 50 is provided to display the configuration of the surface of sample 32 in a scan region. A capacitive display 52 is provided to display, alternatively, the capacitance signal, C, or dC/dV as the tip is scanned across a region of the surface or sample 32 at a selected bias voltage. The selected voltage can be changed and the above quantities can be displayed for those different voltages. One can also measure the capacitance versus voltage at a plurality of separate points and display that on display 52.

Figures 3A, 3B:
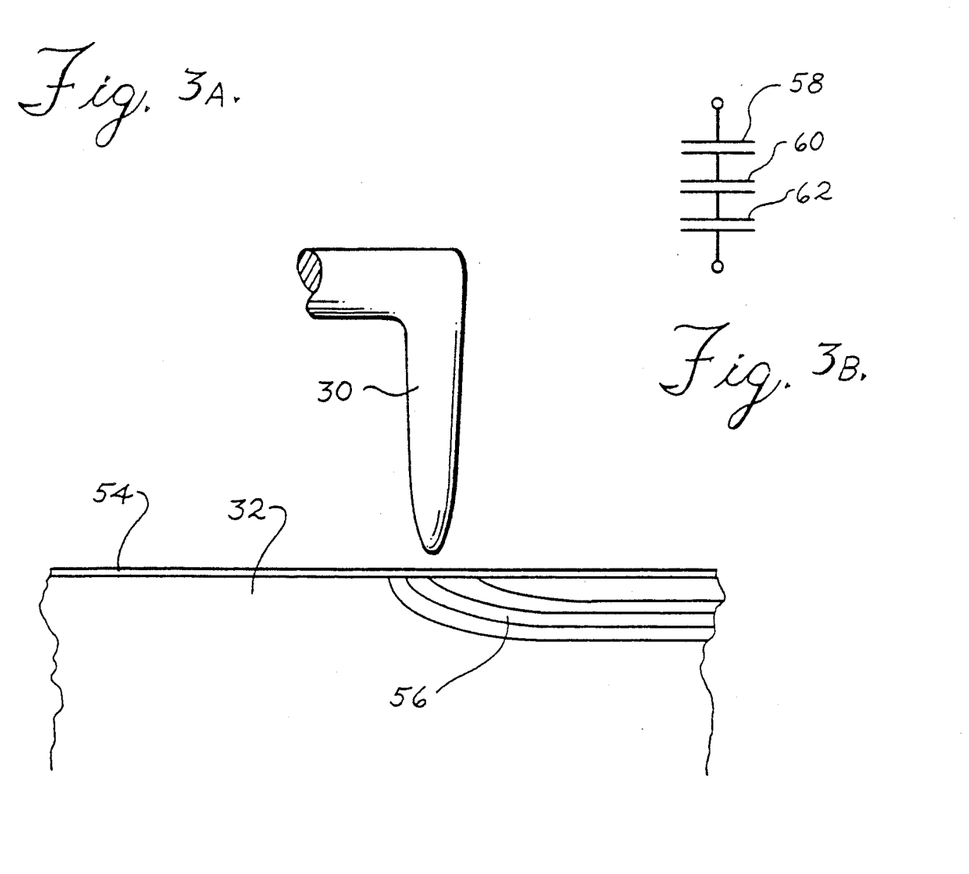

FIG. 3A shows tungsten tip 30, having a radius of curvature at its tip of typically 50 nm, disposed above and very near the top surface of sample 32 on which a thin layer 54 of $SiO_2$ is shown. A region 56 is shown wherein the sample 32 is non-uniformly doped. In accordance with the preferred embodiment of the present invention, a bias voltage (dc or ac) is placed on the tip with respect to the sample, and the local depletion capacitance, or its derivative (dC/dV), are then measured as a function of lateral position. This arrangement produces signals which represent either capacitance or capacitive gradient dC/dZ as a function of bias voltage across the lateral scan path. These signals, which have a high spatial resolution, can be deconvolved to obtain the spatial profile of the local activated dopant density.

As shown in FIG. 3B, such deconvolution involves consideration of three capacitive contributions in series, the capacitance 58 of the air in the vicinity of tip 30, the capacitance 60 of the oxide layer 50, and the capacitance 62 of the sample 32 in the vicinity of tip 30. Deconvolution in accordance with the preferred embodiment is described in detail below.

Figure 4:
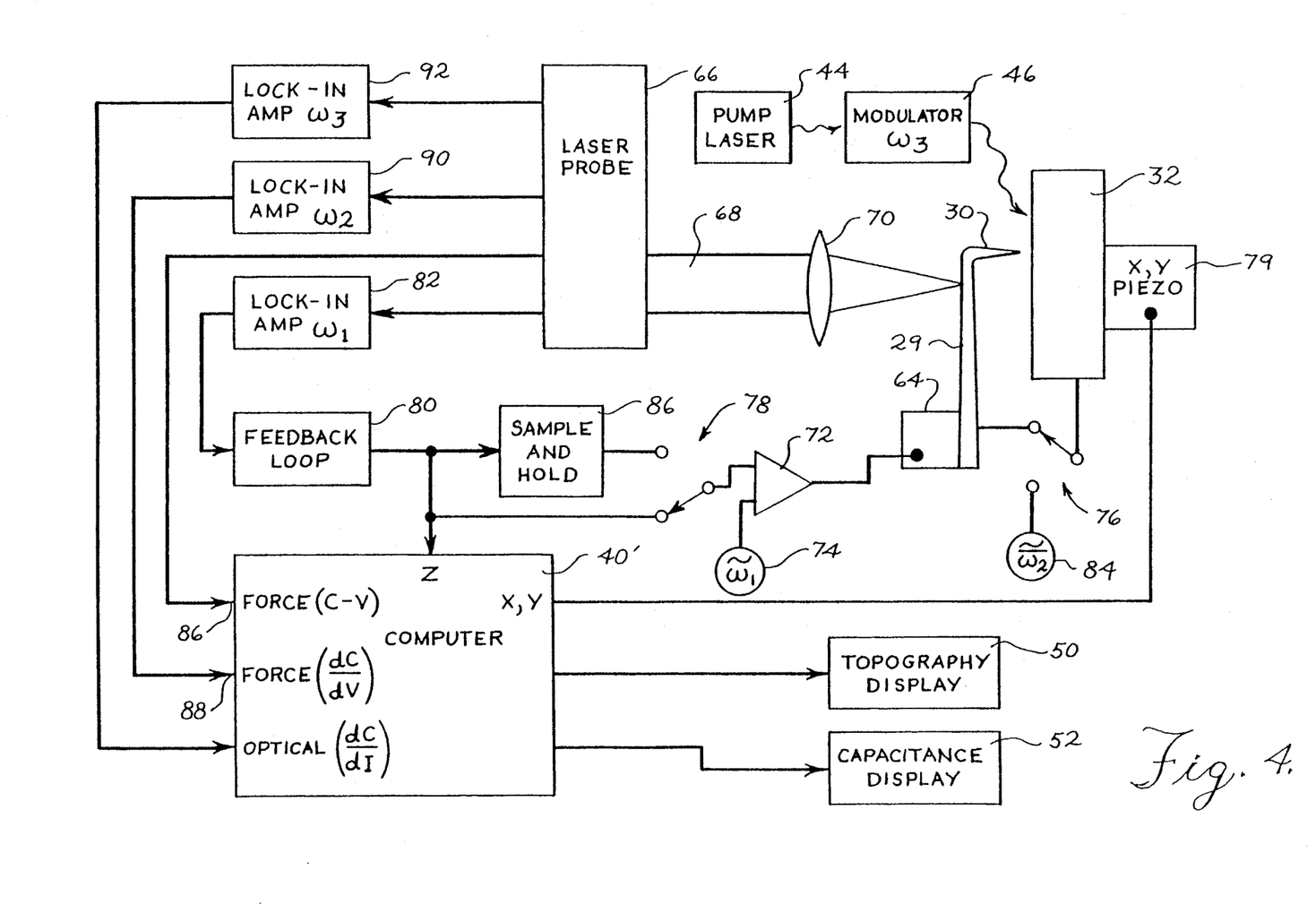
FIG. 4 is a system diagram of a specific implementation of preferred embodiment of the present invention.

FIG. 4 is a schematic diagram of the preferred embodiment of the present invention. It utilizes a laser-heterodyne force microscope, like that described in detail in J. Appl. Phys. 61, 4723 (1987) having certain modifications now described. A fine silicon micromechanical cantilever 29 with a metallic tip 30 is suspended over a sample 32 of semiconductor material. The inventors have used a tungsten wire arrangements for tip 30. Etching of tungsten tips is known in the art for field emission scanning microscopy tips. The inventors have used a similar etching technique to produce long (order 100 microns) cantilevers, being bent at the end to produce a fine tip and force sensing cantilever. Scanning electron microscope images demonstrate the tip diameters could be as small as 50 nm using this technique. This force microscope, used to measure capacitance as set forth herein, can measure capacitive changes between tip and sample on the order of $3 \times 10^{-22}$ F/Hz.

A first piezoelectric crystal 64 is provided for position control of tip 30 in the Z direction, that is, in the direction toward and away from the sample 32. A laser probe 66 generates a laser beam 68 which is focused by way of microscope objective 70 onto a reflective surface of the tungsten tip 30. A sensor (not shown) in laser probe 66 detects the incident laser beam 68 as well as the reflected beam to provide interferometer position information of the tungsten tip 30, according to conventional techniques. A Z feedback signal is generated by lock-in amplifier 82 and feedback loop 80 and provided to a computer 40' and to an amplifier 72 through switch 78 which provides the Z direction control to the first piezoelectric crystal 64. A frequency generator 74 provides an additional signal to amplifier 64 to enable vibration perpendicular to the surface, to maintain a constant gap, as is known in the art. See, for example, Yves Martin, C.C. Williams and H.K. Wickramasinghe, J. Appl. Phys. Vol. 61, 4723 (15 May 1987). The computer display 40' generates XY scanning signals which are provided to a second piezoelectric crystal 79 which controls the XY movement of sample 32 to effect scanning of the tungsten tip 30 across the surface of the sample 32. In the preferred embodiment the second piezoelectric crystal 79 provides a lateral scan range of 100 microns and a vertical scan range of 10 microns.

The system shown in FIG. 4 performs two necessary functions, required to measure dopant through capacitance imaging. The first function required is as mentioned above, to have the ability to move the tip 30 over the sample 32, while maintaining constant the gap between tip and sample. The second function is to measure the local capacitance at each point on the sample.

As mentioned above, maintaining the tip 30 at a constant gap as it is scanned over the sample 32 surface is well known in the art. Briefly, this function is performed with switches 76 and 78 in position 1, the position shown, i.e., the tip 30 and sample 32 are electrically grounded together, and the output of the feedback loop 80 is applied to the summing amplifier 64. In this mode, the tip 30 vertically vibrating at a frequency $\omega_1$ is brought in close proximity of the sample 32. The amplitude of the vibration is modified by the forces between tip and sample. The laser probe 66 and a standard lock-in amplifier 82 tuned to $\omega_1$ measure the amplitude of the vibration, and send a signal to the feedback loop 80 which causes the vertical position of the tip 30 to be moved until the amplitude of the vibration is at the desired level. As the tip 30 is scanned across the surface, the laser probe 66, the lock-in amp 82 and the feedback 80 loop act to maintain the vibrational amplitude to be constant. This condition of constant amplitude is in general found to be equivalent to keeping a constant gap between tip 30 and sample 32.

When measuring capacitance, switches 76 and 78 are moved to position 2, the opposite position to that shown. This allows an ac and/or dc voltage to be placed on the tip 30 with respect to the sample by way of signal source 84. The feedback loop which controls the height of the tip 30 is also disabled, and a sample and hold circuit 86 maintains the tip 30 at the height at which it was found at the time the feedback was disabled, in other words, the tip 30 is "frozen" in its place at the time the two switches 76, 78, 12 are thrown. At that point in time, the applied voltage generator 84 supplies a voltage between tip 30 and sample 32 which is used to measure the local capacitance in several modes. The first mode is the case where the voltage is ramped between a negative voltage, typically $-10$ volts, and a positive voltage, typically $+10$ volts, and the displacement of the tip 30, which is proportional to the force on the tip 30, is measured with the laser probe 66 and sent to the computer 40' at input 86 to be processed. The measured displacement is then related to the local capacitance versus applied voltage as described below. A second mode is where the voltage source 84 supplies both an ac signal and a dc voltage. In general, the ac signal will provide a modulation of the force on the tip 30 at either $\omega_2$ or a harmonic of $\omega_2$, which is sensed by the laser probe 66, and detected by lock-in amplifier 90 preferably at $2\omega_2$, and sent to the computer 40' through input 88, where the laser probe signal can be related to the capacitance variation with voltage (dC/dV), as described below.

Either of these capacitance measurements can be done at a single point, or as the tip is scanned around over the sample. If scanning is done, then the switches 76 and 78 must be placed in position 1, tip 30 moved, switches 76 and 78 must be placed in position 2, voltages applied between tip and sample, measurements sent to inputs 86 and 88 and acquired, switches 76 and 78 placed back to position 1, tip 30 moved, and the above repeated. Topographic variations in the surface may be displayed on display 50. C-V and dC/dV measurements are displayed on display 52.

Laser pump 44 and modulator 46, which modulates at a frequency $\omega_3$, are provided to permit measurement of effects produced by the illumination of 32, as described below. Lockin amplifier 92, tuned to $\omega_3$, provides dC/dI information in this mode, which is sampled at two or more voltages in either step-position or scan mode.

Figure 5:
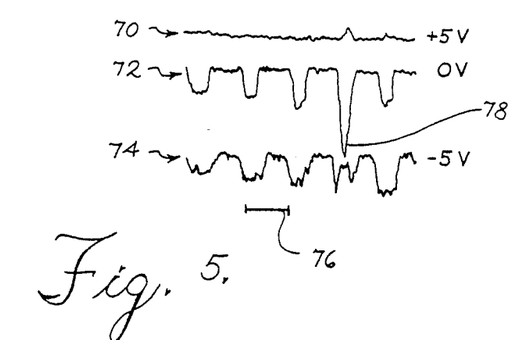
FIG. 5 shows scan traces produced using an embodiment of the present invention.

FIG. 5 depicts the image of the type produced on the second scan synchronized display referred to above, showing dC/dV values at three different bias voltages, $-5V$, $0V$ and $+5V$, determined as the tip 30 of FIG. 4 was scanned across a dopant grating on a first sample in experiments performed to verify the operability of an embodiment of the present invention. Two samples were used in these experiments. Both were n-type silicon substrates with 24 nm of thermally grown oxide on the surface thereof. A dopant grating was generated by a process by which a thick phrtoresist grating structure was masked on the surface of the wafers, with an 8 $\mu$m period, and implanted with $BF_2$ at 50 keV at a dose of $10^{15}$ cm$^{-2}$, producing a peak p-type dopant density at the surface of $10^{20}$ cm$^{-3}$. The photoresist was then stripped, from the surface, leaving a topographically flat, non-uniformly implanted silicon surface covered with 24 nm of thermal oxide. The first wafer sample was thermally annealed at 900° C. for 10 minutes, while the dopant in the second wafer was activated by rapid thermal annealing at 1000° C. for 10 seconds.

From these traces one can effectively "see" the dopant profile in the sample. Distance indicator 76 is 8 $\mu$m in length, corresponding to the 8 $\mu$m photoresist grating structure implanted in the sample. As expected from C-V analysis, this signal varies strongly with the bias voltage. The largest signal comes from the lightly doped region, due to the fact that the capacitance variation with bias voltage, dC/dV, is largest at low dopant densities.

Note the irregular signal spike 78 in the zero bias voltage trace, as well as the corresponding irregularities in the other two traces in FIG. 5. This corresponds to a defect or nonuniformity in the fourth period of the data scan in the figure. This defect or non-uniformity has apparently shifted the depletion voltage. It is possible that this is the result of charge in the oxide.

Figures 6, 8, 9:
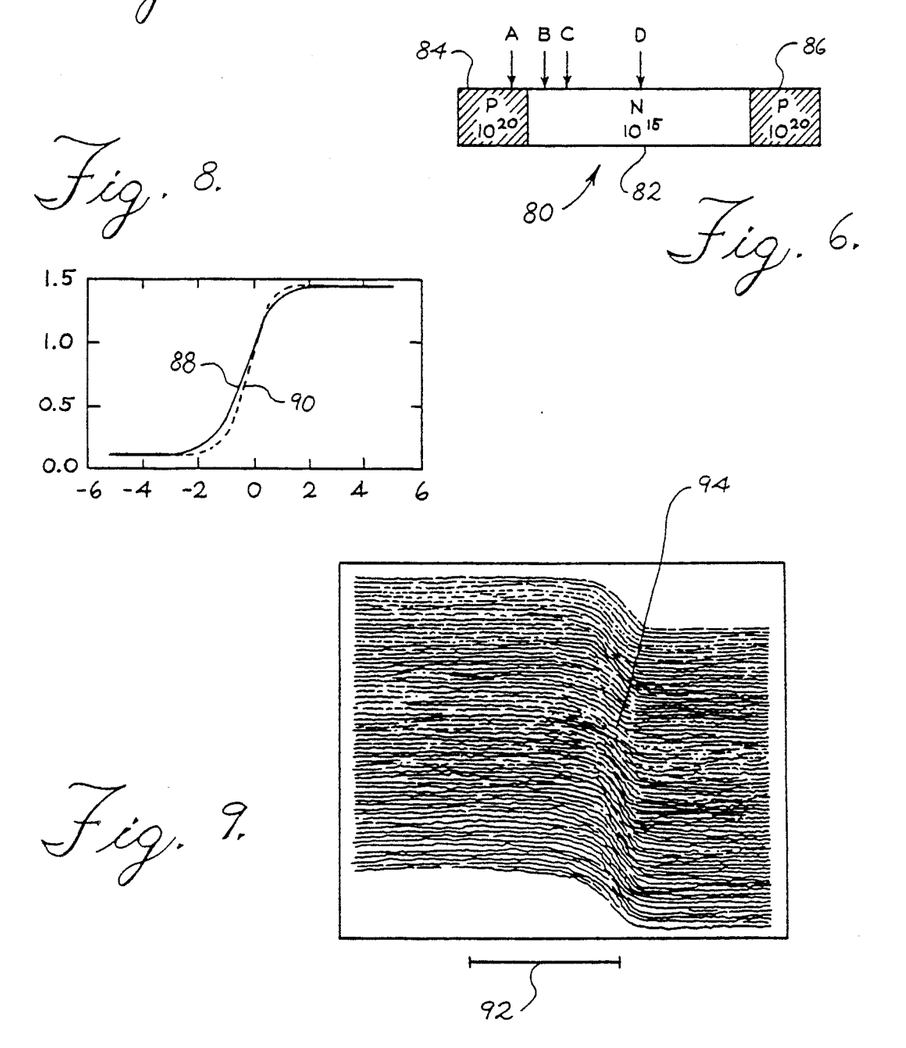
FIG. 6 is a cross sectional diagram of a sample of material used in experiments applying the principles of the present invention.
FIG. 8 is a plot of experimental and theoretical data demonstrating the validity of an embodiment of the present invention.
FIG. 9 shows the scan tracings produced in the application of principles of the present invention to a sample like that shown in FIG. 6.
Figure 7:
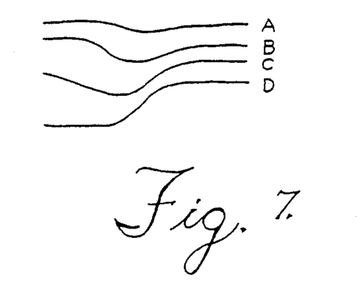
FIG. 7 shows capacitance voltage curves produced at the four points identified in FIG. 6.

FIG. 6 is a cross section through the second sample 80, showing a lightly doped n-type region 82 and a first and a second highly doped p-type region, 84, 86, respectively. Data was taken at points A, B, C, and D shown in FIG. 6. The data taken for this sample 80 were C-V curves, and are shown in FIG. 7 labelled A, B, C and D, corresponding to points A-D, respectively. Curve D, taken at the center of the low doped region, has the same appearance as a classical high frequency C-V curve one might find in a textbook. The other curves in FIG. 7, taken as the scan point was moved toward the implanted region, differ from ideal 1D curves. In fact, a gradual transition in the curves can be seen as the tip moves from the low doped ($10^{15}$ cm$^{-3}$) n-type region toward the highly doped ($10^{20}$ cm$^{-3}$) p-type region. The inventors believe that these effects are the result of lateral depletion of the surface. Thus, even though curves B and C are taken at a distance of greater than 0.5 μm from the implant edge, they are nonetheless, modified by the proximity of the high density dopant region 84. The maximum depletion length in the low, doped region can be calculated, and in sample 80 it was calculated to be 0.87 μm. The data of curves B and C are consistent with this calculation.

Thus, when the probe tip is small compared to this depletion depth, the geometry is more like a spherical than a parallel plate capacitor, and lateral effects can be significant, as in this instance. When the tip is positioned over the highly doped p-type region, and far from the implant edge, the slope of the C-V curve is reversed and much smaller than in the lower case, as predicted by C-V theory. This slope has been measured, but cannot be clearly displayed on the scale of the curves shown in FIG. 7.

When the tip is far from the implant edge, it is expected that even under conditions of spherical depletion, as described above, the C-V curves should be similar to those predicted by one dimensional calculations.

FIG. 8 is a graph showing the super position of an experimentally derived capacitance versus voltage curve 88 against the theoretically calculated curve 90. Considering the finite AC measurement voltage, +/−0.5V, used in the experiments described herein, the fit between 1D theory and experiment is reasonably good.

FIG. 9 is a two dimensional image which was recorded of the dC/dV output, monitored at port B of FIG. 4, at a fixed bias voltage. In this diagram, measurement unit 92 corresponds to 1 μm of scan length. The total scan area is, thus, 3 μm×3 μm. To interpret the image, consider the X and Y axis of the diagram to correspond to the surface of the sample. Consider also that the image has been tilted slightly such that a 3 dimensional image is presented having a slope region 94 from left to right in the diagram. This sloping area represents the transition from low to high doping, and appears to take place on a 200 nm scale.

The method of deconvolving the C-V and dC/dV data to determine impurity dopant density distribution will now be described. In the following, "device" means, referring now to FIG. 3A, the electrical system comprising the probe tip 30, the oxide layer 50, and semiconductor sample 32 being "probed" for C-V and dC/dV data. Two convolution methods may be used: (1) Iteration on simulated versus measured dC/dV data using a device simulator; or (2) iteration using an analytic circuit model to represent the device. Method 2, which is described in detail hereunder, is considered preferred. Method 2 assumes that the device can be represented adequately by an equivalent circuit model.

Method 1, although in principle more accurate since it takes into account 2D or 3D effects by directly solving per charge, carrier and field distributions, requires more computational time. By contrast, Method 2 requires only an IBM ® personal computer with at least an Intel ® 80286 processor, or equivalent, to perform the computations and, in fact, the deconvolution is performed nearly in real time as the data is accumulated.

It was mentioned above in connection with FIG. 4 that a signal corresponding to the force applied to maintain the tungsten tip in relatively constant proximity to the surface of the sample was monitored. The direct relationship between the measured force and the desired capacitive signal is easily understood in the following way. The force, F, on the tip at a bias voltage, V, is $$F = \tfrac{1}{2} V^2 \, dC/dZ. \tag{1}$$

The imposition of a bias, V, at frequency $\omega_2$ with a DC offset, $V_0$, can be represented $$V = V_0 + V_2 \cos(\omega_2 t) \tag{2}$$

where $V_2$ is the AC amplitude. It is clear, then, that there is a component of the force signal at frequency $2\omega_2$ $$F(2\omega_2) = (\tfrac{1}{4}) V_2^2 \, dC/dZ \cos(2\omega_2 t). \tag{3}$$

The amplitude of this force signal is directly proportional to dC/dZ. Under conditions of near-planar depletion in the semiconductor, the probe/sample capacitance is given by (see FIG. 3B, above):

$$C = \frac{1}{(1/C_{ox}) + (1/C_{air}) + (1/C_d)} \tag{4}$$

where
  $C_{ox} = \epsilon_{ox} A, T,$
  $C_{air} = \epsilon_{air} A/Z,$ and
  $C_d = \epsilon_{Sil} A/D,$
where T is the thickness of the oxide layer, Z is the gap distance, that is, the distance between the probe and the top surface of the oxide layer, D is the depletion depth, and $\epsilon_{ox}$, $\epsilon_{air}$ and $\epsilon_{Sil}$ are, respectively, the dielectric constants of the oxide layer, air and silicon.

Given C, as defined in equation (4), the derivative of C with respect to Z will give the relationship between the force on the tip and $C_d$:

$$dC/dZ = (1/\epsilon_{air} A) \left( (T/\epsilon_{ox} A) + (Z/\epsilon_{air} A) + (D/\epsilon_{Sil} A) \right)^{-2} \tag{5}$$

The derivative dC/dZ expressed in equation (5) can now be substituted into equation (3) and the result provides the relationship between the capacitive force on the probe at $2\omega_2$ and the depletion capacitance in the vicinity of the probe, $C_d$. As mentioned above, local dopant density can be derived from the dependence of $C_d$ on voltage.

The probe/sample system for Method 1 can now be understood in terms of a following first-order circuit model. It is to be noted that this first-order model holds only in the "parallel-plate" regime where the probe-to-sample spacing is maintained at a distance less than the screening length of the applied DC bias into the semiconductor. This screening length, or "depletion depth", will vary from around 200 Å to 10,000 Å depending on the local dopant density. Thus, the probe should be controlled to this degree of excursion from the surface, or non-planar screening effects will diminish the accuracy of this deconvolution technique. On the other hand, a more complicated equivalent circuit model than discussed here can be applied as discussed below.

As depicted in FIG. 3B, the probe/semiconducting sample system in air forms a capacitor stack. The total capacitance is the series combination, i.e., equivalent circuit model, of the capacitances due to the probe-air-sample gap, $C_{air}$, the oxide capacitance, $C_{ox}$, and the depletion capacitance of the doped semiconductor, $C_d$. The expression for probe/sample capacitance, C, is given above as equation (4). In actual fact, $C_d$ is also a function of the local carrier concentration which varies in an inhomogeneous fashion in 2D under bias. Again, accounting for such "non-planar" effects requires a more rigorous circuit model.

In the case of inhomogeniously doped sample, i.e. with dopant variations in the lateral (X-Y) and vertical (Z) dimensions, the effective depletion capacitance detected by the scanning capacitance microscope is a function of dopant localized to within roughly a hemispherical region of radius equal to the extent of depletion at a given DC bias. For planar samples with uniform, device-quality oxides, only spatial dopant variations modulate the detected signal. In closed loop operation, dC/dV is measured as a function of lateral position, at a given V. For inhomogeniously doped samples, which vary in dopant density over five orders of magnitude, measurements by the inventors of dC/dV have shown that signal is quite sensitive to local dopant level.

Van Gelder and Nicollian published a method for relating dC/dV to carrier depletion in one dimension, in J. Electrochem. Soc. 118, 138 (1971). In accordance with data deconvolution according to the preferred embodiment of the present invention, this method is extended to permit two dimensional and three dimensional depletion mapping. Given the data dC/dV versus X, the probe lateral position, in accordance with the preferred embodiment, in the planar approximation the local depletion depth, W(X) is a function of local dopant density at X, N(X). If dopant density variation in the third dimension can be neglected, for example if the sample consists of long diffusion stripes, then with the total probe to sample capacitance at position X, $C_t(X)$, determined either by measurement with the scanning capacitance microscope in open loop mode, or by integration of dC/dV data over all values of V from accumulation to depletion of the majority carriers at X, then the following expression can be applied:

$$W(X) = epssi*(1/C_t(X) - 1/C_{ox} - 1/C_{air}).$$

W(X) is actually a measure of the depth Z, to which the mobil carriers have been depleted, exposing ionized dopant atoms of concentration N(X, Z) at that depth. Therefore:

$$N(X, Z = W(X)) = -(C_t^{-3}/(dC_t/dV)/(q*epssi))^{-1},$$

Where q is the electronic charge. Thus, a two dimensional dopant concentration can be obtained. Actual fits to data by the inventors indicate that $C_t(X)$, must be scaled by a constant factor which is unitless and of order unity. This factor scales with the gain of the system and is related to the effective probe spot size presented up to the sample.

Figure 10:
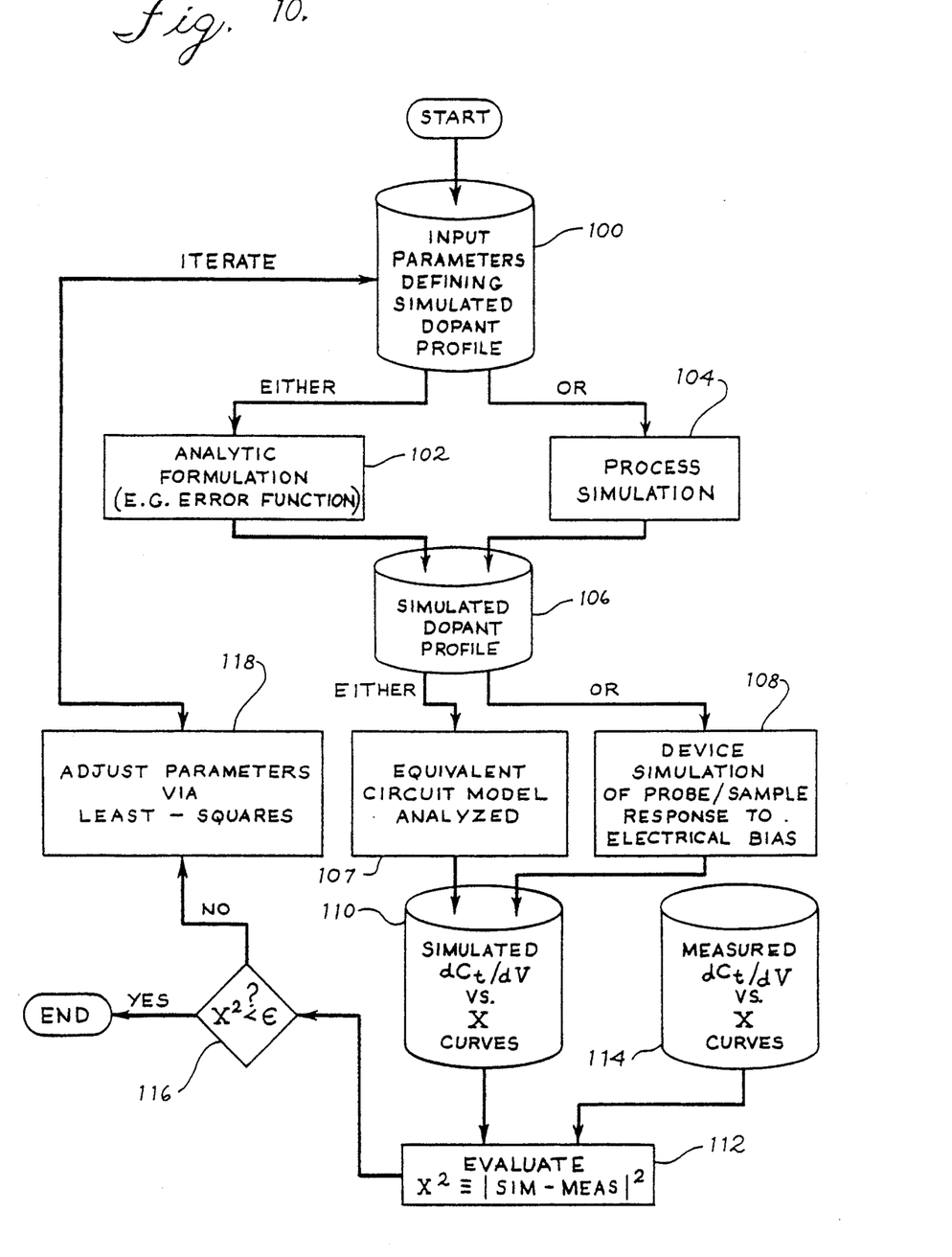
FIG. 10 is a flow chart depicting the deconvolution of measured data to dopant profile data in accordance with the preferred embodiment of the present invention.

Understanding the background for deconvolution described above, refer now to FIG. 10 which is a flow diagram showing in detail the deconvolution of $dC_t/dV$ versus X data to obtain dopant density in three dimensions. The method depicted in FIG. 10 is advantageously implemented by a computer in accordance with standard and well known programming techniques. The basic approach is to simulate a dopant profile using input parameters which are an approximation or "guess" of the profile of the sample to which measurements have been made. These parameters are run against a simulation and compared with measured $dC_t/dV$ versus X data, and the difference is fed back as an adjustment to the input parameters by way of a least-squares algorithm.

In detail, to start the algorithm an approximation of the two or three dimensional profile is required. This can be obtained either by simulation of the VLSI process simulation according to the method described, for example L.J. Borucki, H.H. Hansen, and K. Varahramyan, "FEDSS-A 2-Dimensional VLSI Process Simulator," IBM J. Res. Dev., 1985, or by an analytical approximation, for example an error function profile characterized by a spread or standard-deviation in each of the 3 dimensions. Input parameters defining a simulated dopant profile are provided as input 100 to either an analytic formulation 102 or to a process simulation 104. This yields a simulated dopant profile 106.

The next step in the flow chart of FIG. 10 is that either an equivalent circuit model is analyzed 107, which is preferred, or a device simulation of the response of the probe/sample/air system to the electrical biases applied to the system is performed 108 to obtain simulated $dC_t/dV$ curves 110. The equivalent circuit model was discussed above in connection with FIG. 3B. A detailed description of such a device simulation technique can be found in E.M. Buturla, P.E. Cottrell, B.M. Grossman, and K.A. Salsburg, "Finite Element Analysis of Semiconductor Devices: the FIELDAY Program," IBM J. Res. Dev., 25, 218 (1981).

The above process is iterated until the desired degree of accuracy is obtained, measured by the closeness of fit between the measured $dC_t/dV$ versus X curve data to the iteratively adjusted simulated $dC_t/dV$ versus X curve. The iteratively adjusted input parameters at that point, defining this simulated dopant profile, now correspond to the actual dopant profile of the sample from which the measured data were taken.

While the embodiments described above have been described in connection with determination of impurity dopant profiles in semiconductors, the principals of the present invention may be employed to measure other types of material and electrical properties. For example, in a semiconductor material the capacitance signal will vary depending upon the amount of light which illuminates the semiconductor material. For silicon type semiconductor material, for example, when a one mW laser beam (0.633 nm) is focused onto the tip and sample, both the amplitude of the dC/dV signal and the apparent location of the lateral depletion edge are significantly modified by the light. These effects are due to the creation of electron-hole pairs, which reduce the depletion effect both in the vertical and lateral dimension.

Such measurement can be accomplished using apparatus and techniques as described above, with the addition of a flux meter to monitor the intensity of the laser light. The capacitance signals as a function of the intensity of the laser light is a direct measurement of the electron-hole pair generation and recombination rates.

The technique just described in connection with the measurement of electron-hole pair generation and recombination rates can be applied to measure the local density of defects in semiconductor material, since, as is known, the point and extended defects affect such rates.

Recall that in the discussion in connection with FIG. 5 a defect in the sample produced a significant feature in the dC/dV data. Thus, it is clear that the principles of the present invention may be applied, without optical illumination, to detect the presence of defects.

Thus, it has been shown that in accordance with the preferred embodiment of the present invention lateral dopant profiling in silicon semiconductor material has been achieved on a 200 nm scale non-destructively, and with a technique readily implemented using known apparatus. In addition, the present invention has been shown to be applicable to measurement and depiction of carrier generation and recombination in semiconductor material, as well as subsurface defects, and oxide thickness of such materials. Other material properties may also be measured and depicted once the principles of the present invention set forth herein are understood. Other apparatus, and variations in the methods disclosed herein may be used without departing from the spirit and scope of the invention as set forth herein in the following appended claims.

What is claimed is:

1. A method for determining a property of a material with respect to at least two dimensions, comprising the steps of:

moving a fine tip in close proximity to a surface of said material within a predetermined scan area;

applying a voltage to said tip with respect to said material;

sensing the value of a parameter corresponding to the capacitance in a region of said material near said tip for a plurality of levels of said voltage at a plurality of locations within said scan area;

providing measured data for said locations, said parameter values and said voltage levels; and relating said measured data according to a predetermined relationship to derive said material property at each of the locations, whereby data for said material property is provided with respect to at least two dimensions in the region of said scan.

2. A method according to claim 1, wherein said step of moving said tip is performed by mechanically coupling said material to a piezoelectric motion transducer; and apply a varying voltage to said transducer so as to effect the desired tip motion with respect to said material.

3. A method according to claim 1, wherein:

said step of moving said tip is performed by moving said tip with respect to said material in a scan pattern; and said step of sensing the value of a parameter is performed by sensing such value continually as said tip is scanned, such that said plurality of locations are a continuum of points.

4. A method according to claim 1, wherein said step of sensing the value of a parameter is performed by applying a force to said tip so as to maintain the tip separation from the surface of said material relatively constant; and sensing said force.

5. A method according to claim 1, further comprising the step of oscillating the tip perpendicularly of the material surface when the tip is at a separation distance in close proximity to the sample surface.

6. A method according to claim 5, wherein the step of oscillating the tip is performed at a frequency of one to $10^6$ hertz and at an amplitude in the range of 1 to $10^3$ angstroms.

7. A method for determining dopant density of a semiconductor material with respect to at least two dimensions, comprising the steps of:

scanning a fine tip in close proximity to a surface of said material within a predetermined scan area;

applying a voltage to said tip with respect to said material;

applying a variable force to said tip so as to maintain said tip at a relatively constant spacing from the surface of said material as said tip is scanned;

sensing the magnitude of the variable force for a plurality of said voltage levels at a plurality of locations within said scan area;

providing measured data for said locations, said force magnitude and said voltage levels; and processing said measured data such that the force magnitude data provides capacitance value data of the material in the vicinity of said tip, and the capacitance value data is processed in conjunction with the voltage value data to provide dopant density data for each of the data locations, whereby data for the dopant density is provided with respect to at least two dimensions in the region of said scan.

8. Apparatus for determining a property of a material with respect to at least two dimensions, comprising:

means for moving a fine tip in close proximity to surface of said material within a predetermined scan area;

means for applying a voltage to said tip with respect to said material;

means for sensing the value of a parameter corresponding to the capacitance in a region of said material near said tip for a plurality of of said voltage levels at a plurality locations within said scan area;

means for providing measured data for said locations, said parameter values and said voltage levels; and means for relating said measured data according to a predetermined relationship to derive said material property at each of the locations, whereby data for said material property is provided with respect to at least two dimensions in the region of said scan.

9. Apparatus for determining dopant density of a semiconductor material with respect to at least two dimensions, comprising:

means for scanning a fine tip in close proximity to a surface of said material within a predetermined scan area;

means for applying a voltage to said tip with respect to said material;

means for applying a variable force to said tip so as to maintain said tip at a relatively constant spacing from the surface of said material as said tip is scanned;

means for sensing the magnitude of the variable force for a plurality of of said voltage levels at a plurality of locations within said scan area;

means for providing measured data for said locations, said force magnitude and said voltage levels; and means for processing said measured data such that the force magnitude data provides capacitance value data of the material in the vicinity of said tip, and the capacitance value data is processed in conjunction with the voltage value data to provide dopant density data for each of the data locations, whereby data for the dopant density is provided with respect to at least two dimensions in the region of said scan.

10. A method for determining a property of a material with respect to a least two dimensions, comprising the steps of:
scanning a fine tip in close proximity to a surface of said material within a predetermined scan area;
applying a voltage to said tip with respect to said material;
illuminating the material surface in the vicinity of said tip with a light source of variable intensity;
sensing the value of a parameter corresponding to the capacitance in a region of said material near said tip for one or more levels of light intensity, for a plurality of of of said voltage levels, at a plurality of locations within said scan area;
providing data for said locations, said parameter values, said light intensities and said voltage levels; and
relating said data according to a predetermined relationship to derive said material property at each of the data locations, whereby data for said material property is provided with respect to at least two dimensions in the region of said scan.

11. A method according to claim 10, wherein said step of moving said tip is performed by
mechanically coupling said material to a piezoelectric motion transducer; and
applying a varying voltage to said transducer so as to effect the desired tip motion with respect to said material.

12. A method to claim 10, wherein:
said step of moving said tip is performed by moving said tip with respect to said material in a scan pattern; and
said step of sensing the value of a parameter is performed by sensing such value continually as said tip is scanned, such that said plurality of locations are a continuum of points.

13. A method according to claim 10, wherein said step of sensing the value of a parameter is performed by
applying a force to said tip so as to maintain the tip separation from the surface of said material relatively constant; and
sensing said force.

14. A method according to claim 10, further comprising the step of
oscillating the tip perpendicularly of the material surface when the tip is at a separation distance in close proximity to the sample surface.

15. A method according to claim 14, wherein the step of oscillating the tip is performed at a frequency of one to $10^{}5$ hertz and at an amplitude in the range of $10^{}2$ to $10^{**}6$ angstroms.

16. Apparatus for determining a property of a material with respect to at least two dimensions, comprising:
means for scanning a fine tip in close proximity to a surface of said material within a predetermined scan area;
means for applying a voltage to said tip with respect to said material;
means for illuminating the material surface in the vicinity of said tip with a light source of variable intensity;
means for sensing the value of a parameter corresponding to the capacitance in a region of said material near said tip for one or more levels of light intensity, for a plurality of of said voltage levels, at a plurality of locations within said scan area;
means for providing data for said locations, said parameter values, said light intensities and said voltage levels; and
means for relating said data according to a predetermined relationship to derive said material property at each of the data locations, whereby data for said material property is provided with respect to at least two dimensions in the region of said scan.

17. A method for determining a property of a material with respect to at least two dimensions, comprising the steps of:
scanning a fine tip in close proximity to a surface of said material within a predetermined area;
applying a voltage to said tip with respect to said material;
sensing respective values of a parameter corresponding to the capacitance in a region of said material near said tip for a plurality of of said voltage levels at respective ones of plurality of locations within said area;
relating said respective values and voltage levels according to a predetermined relationship to derive said material property at each of said respective ones of said plurality of locations, whereby data for said material property is provided with respect to at least two dimensions within said predetermined area.

18. A method for determining a property of a material with respect to at least two dimensions, comprising the steps of:
moving a fine tip in close proximity to a surface of said material within a predetermined scan area;
applying a voltage to said tip with respect to said material;
sensing the value of a parameter corresponding to the capacitance in a region of said material near said tip for a plurality of of said voltage levels at a plurality of locations within said scan area;
providing measured data for said locations, said parameter values and said voltage levels; and
relating said measured data according to a predetermined relationship to derive said material property at each of said locations, by
providing deriving means for deriving data for said parameter values and said voltage levels for said locations, from data corresponding to said property at said locations,
providing input data corresponding to the estimated property values at said locations to said deriving means, and deriving first estimated data for said parameter values and said voltage levels for said locations,
comparing said estimated data with said measured data,
modifying said input data based on the results of said step of comparing, to derive input data corresponding more closely to the actual property values of said material, and
repeating said steps of providing input data, comparing and modifying until said estimated data and said measured data differ by no more than a preselected factor, whereby data for said material property is provided with respect to at least two dimensions in the region of said scan.

19. A method for determining a property of material with respect to at least two dimensions, comprising the steps of:

scanning a fine tip in close proximity to a surface of said material within a predetermined area;

applying a voltage to said tip with respect to said material;

sensing respective values of a parameter corresponding to the capacitance in a region of said material near said tip for one or more of said voltage levels at respective ones of a plurality of locations within said area, by applying a first force to maintain said tip at a relatively constant distance from the surface of said material, and sensing a second force generated between said tip and said material;

relating said respective values and voltage levels according to a predetermined relationship to derive said material property at each of said respective ones of said plurality of locations, by relating said second force to a capacitance of said material in the vicinity of said probe by the formulas $$C = \frac{1}{(1/Cox) + (1/Cair) + (1/Cd)}$$

where
$Cox = \epsilon_{ox} A/T$,
$Cair = \epsilon_{air} A/Z$, and
$Cd = \epsilon_{Sil} A/D$, where T is the thickness of the oxide layer, Z is the distance between the probe and the top surface of the oxide layer, D is the depletion depth, and $\epsilon_{ox}$, $\epsilon_{air}$ and $\epsilon_{Sil}$ are, respectively, the dielectric constants of the oxide layer, air and silicon, and $$F = \tfrac{1}{2} V^2 \, dC/dZ$$

where F is said second force, V is said applied voltage where, and dC/dZ is the rate of change of the capacitance of the tip and material system, including surrounding air, whereby data for said material property is provided with respect to at least two dimensions within said predetermined area.

* * * * *